(12) United States Patent
Harari et al.

(10) Patent No.: US 11,344,325 B2
(45) Date of Patent: May 31, 2022

(54) RETRIEVAL SYSTEM

(71) Applicant: CERETRIVE LTD., Misgav (IL)

(72) Inventors: Shahar Harari, Tel Aviv (IL); Tanhum Feld, Merhavya (IL); Maysa Mustafa, Zichron Yaakov (IL)

(73) Assignee: CERETRIVE LTD., M.P Misgav (IL)

( * ) Notice: Subject to any disclaimer, the term of this patent is extended or adjusted under 35 U.S.C. 154(b) by 0 days.

(21) Appl. No.: 16/644,244

(22) PCT Filed: Sep. 28, 2018

(86) PCT No.: PCT/IL2018/051074
§ 371 (c)(1),
(2) Date: Mar. 4, 2020

(87) PCT Pub. No.: WO2019/064306
PCT Pub. Date: Apr. 4, 2019

(65) Prior Publication Data
US 2021/0059695 A1    Mar. 4, 2021

Related U.S. Application Data

(60) Provisional application No. 62/676,993, filed on May 27, 2018, provisional application No. 62/566,388, filed on Sep. 30, 2017.

(51) Int. Cl.
*A61B 17/221*   (2006.01)
*A61F 2/01*   (2006.01)
*A61B 17/22*   (2006.01)

(52) U.S. Cl.
CPC ............ *A61B 17/221* (2013.01); *A61F 2/013* (2013.01); *A61B 2017/22001* (2013.01);
(Continued)

(58) Field of Classification Search
CPC .............. A61B 17/221; A61B 17/3207; A61B 17/12177; A61B 17/22031;
(Continued)

(56) References Cited

U.S. PATENT DOCUMENTS

2004/0122468 A1* 6/2004 Yodfat ...................... A61F 2/01
606/200
2006/0047286 A1   3/2006 West
(Continued)

FOREIGN PATENT DOCUMENTS

WO   2017072761 A1   5/2017

OTHER PUBLICATIONS

Int'l. Search Report for PCT/IL2018/051074, dated Jan. 13, 2019.

*Primary Examiner* — Wade Miles
*Assistant Examiner* — Kankindi Rwego
(74) *Attorney, Agent, or Firm* — Blue Filament Law PLLC

(57) ABSTRACT

A system for retrieving material or objects from a biological vessel is provided. the system includes an elongated braid structure configured for transitioning between collapsed and expanded states, the elongated braid structure surrounding a lumen having a distal opening when in the expanded state. The system further includes a closure wire positioned along a length of the elongated braid structure, the closure wire being actuatable to pull inward a distal portion of the elongated braid structure and thereby at least partially close the distal opening.

15 Claims, 15 Drawing Sheets

(52) U.S. Cl.
CPC ............... *A61B 2017/2215* (2013.01); *A61B 2017/2217* (2013.01); *A61B 2017/22035* (2013.01)

(58) Field of Classification Search
CPC ........... A61B 2017/00287; A61B 2017/22001; A61B 2017/22044; A61B 2017/22035; A61B 2017/22045; A61B 2017/22049; A61B 2017/22094; A61B 2017/2212; A61B 2017/2215; A61B 2017/2217; A61F 2/01; A61F 2/013; A61F 2002/016
USPC ....................................................... 606/127
See application file for complete search history.

(56) References Cited

U.S. PATENT DOCUMENTS

| | | | |
|---|---|---|---|
| 2006/0155305 A1* | 7/2006 | Freudenthal | A61B 17/221 606/114 |
| 2006/0195118 A1* | 8/2006 | Richardson | A61B 17/221 606/113 |
| 2014/0257362 A1* | 9/2014 | Eidenschink | A61F 2/01 606/200 |
| 2014/0257632 A1 | 9/2014 | Kanzaki et al. | |

* cited by examiner

RETRIEVAL SYSTEM

BACKGROUND

The present invention relates to a system for retrieving material or objects from a biological vessel and methods of using same. Embodiments of the present invention relate to a system having an elongated braid structure capable of grasping or trapping material such as clots or objects such as stents positioned within a biological vessel. Procedures for unblocking biological vessels such as arteries are well known in the art and typically employ minimally invasive devices capable of opening, disintegrating or removing the material blocking the vessel lumen.

Traditional clot removal devices used in, for example, treatment of ischemic stroke or pulmonary embolism employ suction for aspirating clot material.

Although such aspiration devices are effective in retrieving small clots, aspiration of large clots can lead to clot fragmentation and release of potentially harmful clot particles into the blood stream.

In recent years, significant advances have been made in the field of mechanical thrombectomy devices that are designed for mechanically trapping and retracting clot material from the vasculature.

However, despite advances made in mechanical thrombectomy, there is still room for improvement particularly in clot engagement and retraction with minimal clot fragmentation.

There is thus a need for, and it would be highly advantageous to have, a retrieval system that can effectively arrest flow in a vessel and trap, encapsulate and remove blockage material while minimizing clot fragmentation.

SUMMARY

According to one aspect of the present invention there is provided a system for retrieving material or objects from a biological vessel comprising an elongated structure configured for transitioning between collapsed and expanded states, the elongated structure surrounding a lumen having a distal opening when in the expanded state; and a closure wire positioned along a length of the elongated structure, the closure wire being actuatable to pull inward a distal portion of the elongated structure and thereby at least partially close the distal opening; wherein the closure wire is positioned such that the distal portion of the elongated structure is not pulled inward when the elongated structure is bent along the length.

According to embodiments of the present invention the elongated structure is an elongated braid structure.

According to embodiments of the present invention the elongated braid structure decreases in length when expanded.

According to embodiments of the present invention the closure wire is spiraled along the length of the elongated braid structure.

According to embodiments of the present invention the distal portion of the elongated braid structure includes eyelets and further wherein the closure wire runs through at least some of the eyelets.

According to embodiments of the present invention the elongated braid structure includes a plurality of helically wound wires crossing a plurality of counter-helically wound wires.

According to embodiments of the present invention the at least some of the plurality of helically wound wires cross the plurality of counter-helically wound wires at an angle of 70-120 degrees.

According to embodiments of the present invention the distal end of the elongated braid structure forms a plurality of wire loops.

According to embodiments of the present invention a plane of the eyelets is different from the plane of the wire loops According to embodiments of the present invention each of the plurality of wire loops interconnects a helically wound wire to a counter-helically wound wire.

According to embodiments of the present invention the plurality of wire loops cross each other.

According to embodiments of the present invention the system further comprises a catheter attached to the elongated braid structure.

According to embodiments of the present invention the elongated braid structure is maintainable in the collapsed state within a distal portion of the catheter.

According to embodiments of the present invention the distal portion of the catheter includes a sheath and the elongated braid structure self-expands when the sheath is retracted.

According to embodiments of the present invention the elongated braid structure is sized for positioning within a blood vessel.

According to embodiments of the present invention the elongated braid structure includes a cover.

According to embodiments of the present invention the cover is fabricated from polyurethane or PTFE.

According to embodiments of the present invention the closure wire is trapped between the braid structure and the cover or embedded within the cover.

According to embodiments of the present invention the elongated braid structure is capable of applying suction at the distal opening.

According to embodiments of the present invention the system further comprises a vacuum source in communication with the lumen of the elongated braid structure.

According to embodiments of the present invention the wire is positioned within a tube running the length of the elongated braid structure.

According to embodiments of the present invention a wire portion forming a loop of the plurality of wire loops is more compliant than a second wire portion forming the elongated braid structure proximal to the plurality of wire loops.

According to embodiments of the present invention the closure wire is attached to at least one eyelet of the eyelets.

According to embodiments of the present invention each of the plurality of wire loops angles outward from the distal opening.

According to another aspect of the present invention there is provided a system for retrieving material or objects from a biological vessel comprising an elongated braid structure configured for transitioning between collapsed and expanded states, the elongated braid structure surrounding a lumen having a distal opening when in the expanded state; wherein the elongated braid structure includes a plurality of helically wound wires crossing a plurality of counter-helically wound wires forming a plurality of wire loops around the distal opening of the elongated braid structure.

According to embodiments of the present invention each of the plurality of wire loops interconnects a helically wound wire to a counter-helically wound wire.

According to embodiments of the present invention the plurality of helically wound wires cross the plurality of counter-helically wound wires at an angle of 70-120 degrees.

According to embodiments of the present invention the elongated braid structure is sized for positioning within a blood vessel.

According to yet another aspect of the present invention there is provided method of retrieving material or an object from a biological vessel, positioning within the biological vessel the system; drawing the material or object into the lumen; and at least partially closing the distal opening of the elongated braid structure.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION

Figure 1A:
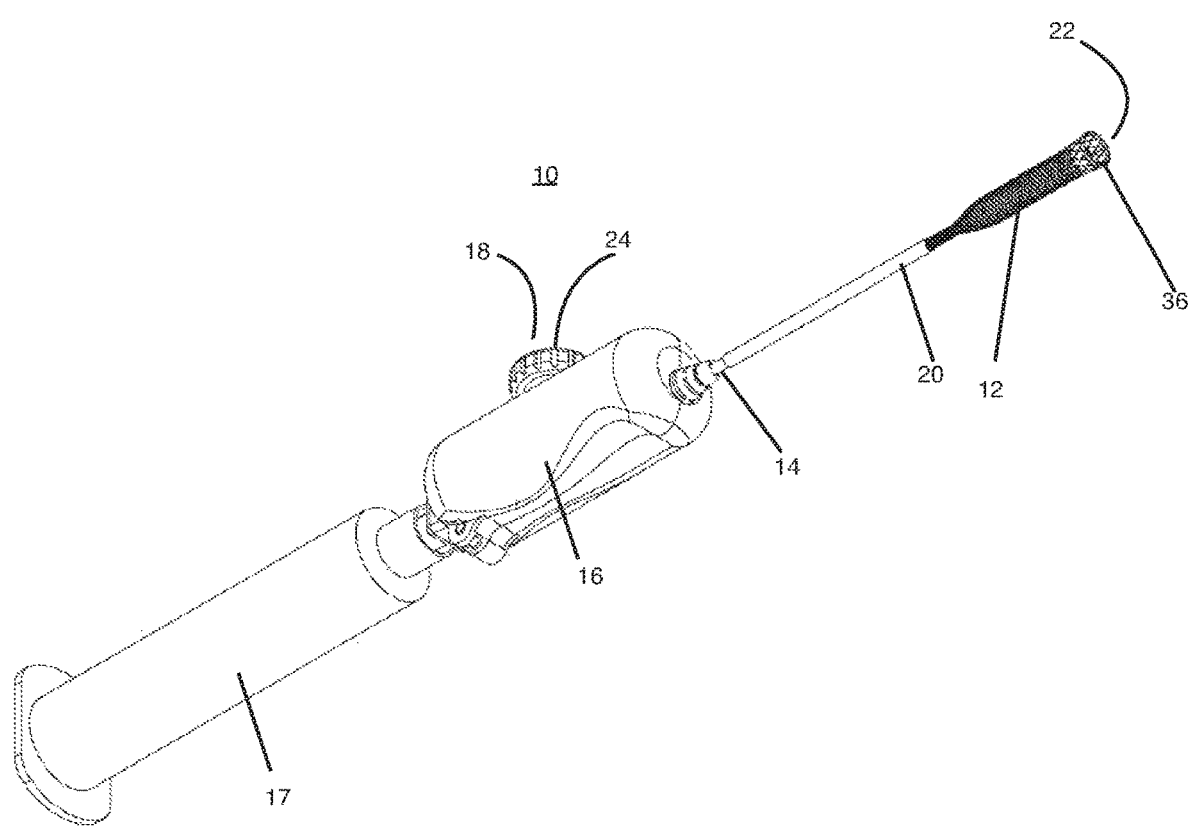
FIG. 1A is an isometric view of one embodiment of the present system.

The present invention is of a system which can be used for retrieving material and objects from a biological vessel. Specifically, embodiments of the present invention can be used to retrieve clots from blood vessels while minimizing clot fragmentation.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Mechanical thrombectomy devices that utilize sleeve-like traps for retrieving clot material are well known in the art. Such traps can include a closable distal opening for maintaining the retrieved clot within the sleeve and minimizing release of clot or fragments from the sleeve when it is pulled out of the vasculature. Closure mechanisms of sleeve-type traps can reduce the effective diameter of the distal opening thereby reducing the maximum size of clot that can be retrieved by such sleeves.

While reducing the present invention to practice, the present inventors set out to provide a mechanical thrombectomy system that is capable of maximizing clot retrieval while minimizing clot fragmentation. The present system includes an elongated braid structure formed with a closable distal end capable of trapping clot material within the braid structure. The elongated braid structure is configured for transitioning between collapsed and expanded states in which a distal opening adjusts to the diameter of a vessel lumen thereby maximizing retrieval of large clots while minimizing fragmentation. The elongated braid also includes a closure mechanism that is unaffected by longitudinal bends in the elongated braid structure and does not reduce the diameter of the distal opening while enabling complete closure and optionally internal inversion of the distal opening.

Thus, according to one aspect of the present invention there is provided a system for retrieving material or objects from a biological vessel.

As used herein, the term "material" refers to a biological material such as a thrombus/clot, stones or the like while the term "object" refers to an implant such as a stent, stent-graft and the like.

Any biological vessel can be accessed and treated using the present system, examples include vessels of the vasculature (e.g., arteries, veins), vessels of the urinary tract (e.g., urethra, ureters) and vessels of the brain.

The system of the present invention includes an elongated braid structure configured for transitioning between collapsed and expanded states. When in the expanded state the elongated braid structure can be shaped as a cylinder/sleeve/funnel having a lumen accessible via a distal opening. When collapsed, the elongated braid structure is a narrow cylinder having a small lumen (large enough for threading of a guidewire and microcatheter). The elongated braid structure can be self expanding in which case it will self expand to a final diameter that is limited by a diameter of the vessel (up to a diameter limited by the braid structure).

According to one embodiments of the present invention, the elongated braid structure can be fabricated from metallic (e.g. stainless steel or NITINOL) or polymeric (e.g., PTFE) wires that are braided in alternating helical and counter-helical directions. The diameter of the wire can be between 0.04-0.08 mm while the braid angle between wires can range between 70-140 degrees.

The parameters and dimensions of the device depend on use and type of vessel. When used in ischemic stroke applications in an intra-cranial artery, the target artery size could vary between 2.5-4.5 mm. The expandable braid structure diameter should be at least slightly larger than the vessel diameter to arrest blood flow, and would therefore range between 2-7 mm. The length of the expandable braid structure should be long enough to support receiving long clots, but short enough to allow pulling the removable sheath to deploy the expandable braid structure with minimal force (typically 10-60 mm or 20-40 mm). The pull force for pulling the removable sheath is equivalent to the expandable braid structure length. Anatomical tortuosity of the blood vessel further increases the pull force. Another benefit to a shorter expandable braid structure is that it reduces the probability of occlusion of side branches.

The elongated braid structure can be fabricated using a mandrel of suitable size by wrapping wires in an alternating helical pattern. For example, a single wire can be looped and the tails of the loop can be wrapped in a helical pattern around the mandrel so as to form a crisscrossing pattern in every wire (1×1 pattern) or crisscrossing pattern every 2 wires (2×1 pattern) along the length of the mandrel. Several wires (12-64) can be used to form the braided structure. An example of such braiding is provided in the Examples section that follows.

The present system also includes a catheter for delivering the elongated braid structure into the vessel. According to one embodiment of the present invention, the elongated braid structure can be attached to a distal end of the catheter shaft and covered by a removable sheath when in the collapsed configuration. Removal (pulling in proximal direction) of the sheath can deploy the elongated braid structure.

In another embodiment of the present invention the elongated braid structure is trapped in a collapsed state in a lumen of the catheter shaft and is pushed out for deployment.

The elongated braid structure can also be configured for deployment via a balloon. In such a configuration expansion of the elongated braid structure requires inflation of a removable balloon therein.

As is mentioned hereinabove, the distal opening of the elongated braid structure is closable via a closure mechanism.

According to one embodiment of the present invention the distal end of the elongated braid structure is configured with looped ends that form leaflet-like closure flaps.

When in the open position, the loops can be positioned in the same plane as the wall of the braid structure or they can be angled with respect thereto. For example, the loops can angle outward 10-30 degrees. Such angling decreases the likelihood that the leaflets obstruct collection of a clot or unwantedly deflect inward during collection.

The wire portion forming the loops can be identical to a second wire portion forming the rest of the braid structure or it can be more compliant than the second wire portion. Increased compliance can be achieved using a thinner wire or a wire of different characteristics (e.g. made from a different material) or different braiding pattern—less dense than that of the braid structure (e.g., 0.5 mm length of the rib/wire for loops and 3 mm length of diamond rib for braid structure). Making the loops more compliant enables closure without applying bending forces to the elongated braid structure when, for example, a pull wire is used to close the leaflets.

A closure wire running the length of the elongated braid structure (and catheter) is threaded through these loops or through eyelets formed therein (e.g., by twisting the end of the loops) or attached thereto. The eyelets can be positioned in the same plane as the loops or they can be angled with respect thereto (10-90 degrees). When pulled, the wire pulls (elastically bends) the loops inward into the center of the distal opening thereby closing it. According to one embodiment of the present invention the wire and loops can be configured such that further pull on the wire following closure can cause inversion of the loops into the lumen of the elongated braid structure, i.e. the closed distal end is pulled proximally and into the lumen of the elongated braid structure. Such a feature is advantageous in that it provides longer operative length for pulling the closure wire. Inversion is also beneficial for securing the clot inside the braid structure and minimizes extrusion of the clot from the braid structure. Extrusion forces can be applied to the clot while attempting to pull the braid structure back into the guiding catheter or guiding sheath.

The closure (pull) wire can be a metallic or polymeric wire made from one or more filaments. The diameter of the wire can be 0.02-0.25 mm. The wire can be freely positioned along the length of the braided structure or trapped within a conduit (e.g. polymeric tube or braided tube within the sleeve braid structure).

According to an embodiment of the present invention the closure wire is positioned along a length of the elongated braid structure such that bending of the elongated braid structure along its longitudinal axis does not pull the loops inward and close the distal opening.

The elongated braid structure length increases when constrained into the outer sheath. The pull wire axial length inside the elongated braid structure and the elongated braid structure length should be similar in order to allow both to compress and expand together. If the pull wire axial length does not increase together with the elongated braid structure length when compressed, the pull wire will be stretched to pull the loops inward and may damage the loops and interfere with compression.

According to one embodiment of the present invention this problem can be overcome by creating a nonlinear route for the pull wire inside the elongated braid structure that changes its axial length together with the elongated braid structure. Such a nonlinear route is preferably helical (e.g. spiral or corkscrew) but can also be a meandering curve.

According to an embodiment of the present invention the distal end of the pull wire is shaped as a circle (threaded through the loops or eyelets). Such a circular wire portion reinforces the loops and increase their radial resistance. Using the pull wire for this purpose is very efficient since it applies a radial force to the loops at their distal end creating maximal outward torque on the loops.

In alternative embodiment, the pull wire is spiraled along the braid structure threaded through the loop eyelets one or more revolutions and then spiraled back into the braid structure and attached to the pull wire in the shaft lumen.

The pull wire can also be fabricated from a soft material at its distal portion (where it engages the loops), such that it does not substantially resist loop expansion when the elongated braid structure expands. For example, the pull wire can be constructed from more than one material—a Nitinol wire along the length of the catheter and braid structure and a polymer extension at the distal portion for engaging the loops.

Since the elongated braid structure is used for trapping clot material that can fragment and release into the blood stream it is preferably covered with a cover fabricated from polyurethane, PTFE, or the like. The cover prevents escape of particles from the lumen of the elongated braid structure and facilitates application of a suction therethrough if needed.

In an embodiment of the present system that includes a cover, the pull wire can be routed between the cover and inner/outer wall of the braid or through a tube having a diameter of 0.05-0. 5 mm which is routed between the cover and inner/outer wall of the braid.

The wire loops can be actuated between closed and open positions using an electric current provided to the loops. When the electric charge on the loops is modified by the current it actuates movement of the loops. The electric charge is applied by a metal wire extending from the proximal end of the catheter to the distal opening of the leaflets, passing through isolated lumen, and connected to dedicated power source in the proximal end.

According to another embodiment of the present invention the distal end of the elongated braid structure is configured with elongated wire segments that include eyelets. Such wire segments can be extension of the braid structure or they can be formed from the pull wire.

The present system also includes a handle attached to a proximal end of the catheter shaft. The handle includes controls for actuating deployment of the elongated braid structure and closure of the distal opening. Alternatively, the handle can include controls for the closure of the distal opening while the deployment of the elongated braid structure can be achieved by simply retracting the proximal end of the sheath separately from the handle. The handle can be attached to a source of suction (e.g., syringe, pump).

As is mentioned hereinabove, the present system can be configured for retrieval of materials or objects from any biological vessel.

The present system is particularly useful for retrieval of clots from blood vessels. An Example of such a system is described below.

Figure 1B:
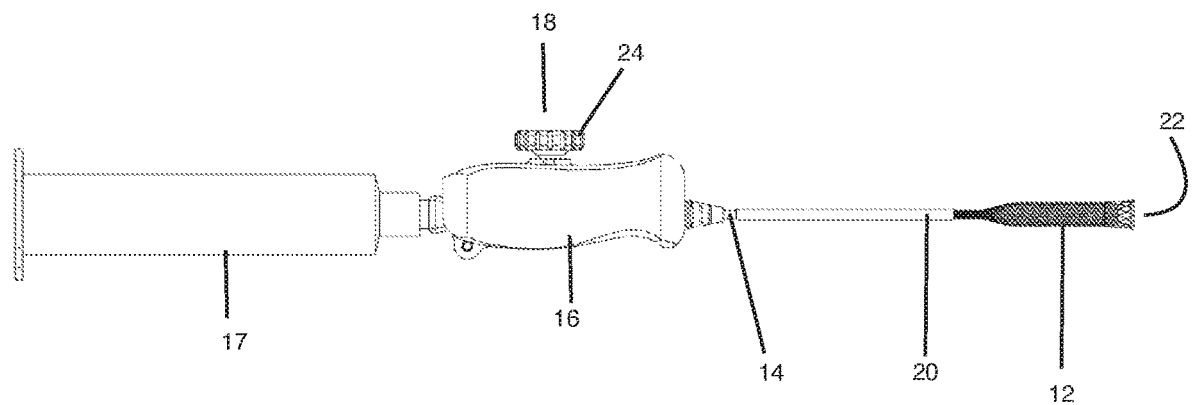
FIG. 1B is a side view of one embodiment of the present system.

Referring now to the drawings, FIGS. 1A-B illustrate a clot retrieval system which is referred to herein as system 10.

System 10 includes (distal to proximal) an elongated braid structure 12 (shown in expanded state) attached to a distal end of a catheter shaft 14 with the proximal end of the catheter shaft attached to a handle 16.

Handle 16 can be connected to the sheath 20 and include controls 18 for actuating expansion of elongated braid structure 12 by, for example, pulling back a sheath 20 (shown pulled back in FIG. 1A) or by pushing elongated braid structure 12 out of sheath 20 and for actuating opening and closing of distal opening 22 of elongated braid structure 12. A distal end of sheath 20 can be positioned out of the body proximally to handle 16 (e.g. 5 cm). Pulling/pushing the exposed distal end of sheath 20 with respect to catheter shaft 14 controls expansion/collapse of braid structure 12. Alternatively, elongated braid structure 12 can be pushed out of sheath 20 using a plunger/push-wire mechanism.

Controls 18 can include a knob 24 for pulling the pull (closure) wire connected to the leaflets through a small lumen in shaft. Controls 18 can also include a slider for pulling back sheath 20 or pushing elongated braid structure 12.

Handle 16 can be attached to a suction source 17 for applying suction at elongated braid structure 12. Suction source 17 can be a syringe (as is shown in FIGS. 1A-B) or a pump. Suction source 17 is fluidly connected to a lumen of elongated braid structure through an aspiration lumen positioned within catheter shaft 14.

Handle 16 can be fabricated from a polymer in a shape suitable for holding and operating knob 24.

Catheter shaft 14 can be an elongated hollow tube connecting handle 16 to braid structure 12. Catheter shaft 14 is selected of a length, diameter and flexibility suitable for the intended treatment location. Different anatomical locations will require catheter shafts 14 of different stiffness and axial flexibility. Catheter shafts 14 having variable stiffness and axial flexibility along the shaft length are well known in the art. Such shafts can be braided or coiled shafts that include an internal polymer shaft with a low friction layer such as PTFE, metal braiding or coil over the internal layer, and an external polymer layer (jacket) such as PEBAX or polyamide composites with various durometer ratings. These type of shaft are commonly used for delivery into tortuous vasculature or intra-cranial vasculature.

Catheter Sheath 20 can be an elongated hollow tube capable of sliding over shaft 14 and the elongated braid structure 12. The length of sheath 20 can be shorter than the combined length of shaft 14 and braid structure 12 to enable pulling the sheath back for expansion of braid structure 12. The sheath can be pulled by a sheath pull wire deployable from the handle. Pullback of the sheath exposes the elongated braid structure 12 which self-expands to occupy the vessel lumen.

Catheter sheath 20 is selected of a length, diameter and flexibility suitable for the intended treatment location. Requiring high distal flexibility and trackability performances, achieved by selecting soft material jacket and metal coil design. The sheath 20 function for delivery in tortuous anatomy and proximal stiffness and pushability require catheter sheath 20 of different stiffness and axial flexibility. Catheter sheath 20 having variable stiffness and axial flexibility along the sheath length are well known in the art. Such catheter can be braided or coiled that include an internal polymer shaft with a low friction layer such as PTFE, metal braiding and coil in different sections over the internal layer, and an external polymer layer (jacket) such as PEBAX, polyurethane or polyamide composites with various durometer ratings.

Typically, the proximal region of the shaft is relatively stiff in order to maximize column force transmission, with stiffness gradually reducing and flexibility increasing towards the distal region so as to enable routing through torturous anatomy.

Catheter shaft 14 can include an aspiration conduit to accommodate aspiration from suction source 17. The aspiration conduit can also be used for deploying elongated braid structure 12 by using it to push elongated braid structure 12 out of sheath 20. Catheter shaft 14 can also include a second lumen for accommodating an actuation wire for closing/opening distal opening 22. The aspiration conduit and wire lumen can be round, rectangular or crescent-shaped.

The outer diameter of catheter shaft 14 can be 1.5-3 mm (e.g., 1.9 mm), while the inner diameter of the catheter shaft which is the aspiration conduit can be 1.2-2.8 mm. The pull/closure wire lumen can be 0.02-0.20 mm in diameter.

The length of catheter shaft can range anywhere between 10-180 cm and is selected according to the target vessel and location treated.

Figure 2A:
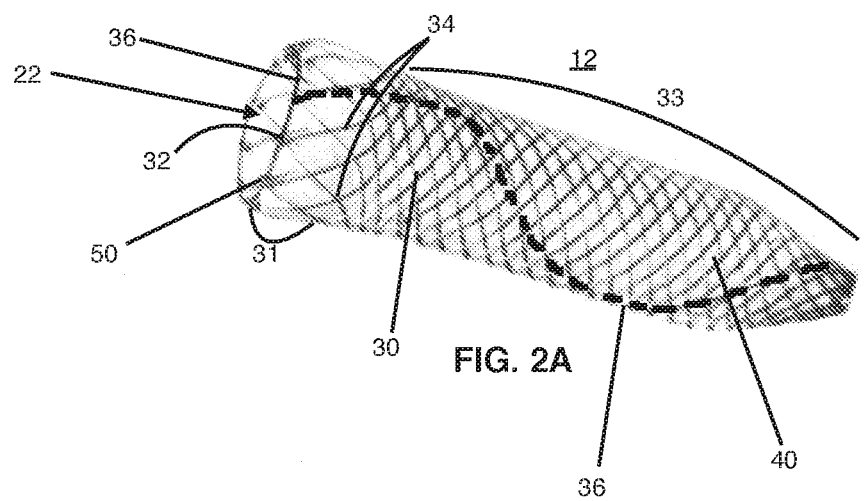
FIG. 2A is an isometric view of one embodiment of the elongated braid structure shown in an expanded open state.
Figure 2B:
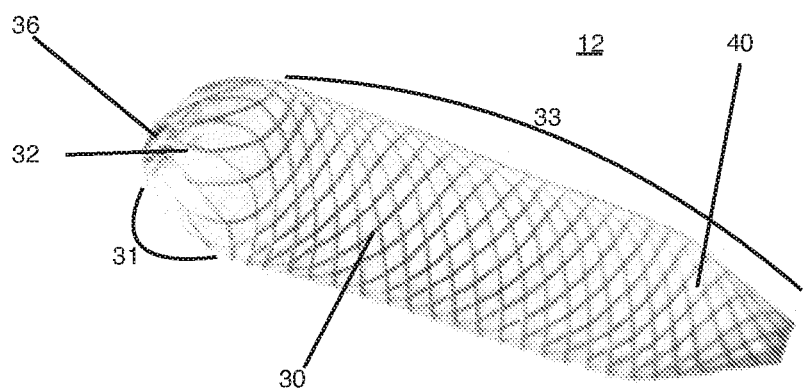
FIG. 2B is an isometric view of one embodiment of the elongated braid structure shown in a closed state.

FIGS. 2A-B show elongated braid structure 12 in more detail. When expanded, elongated braid structure 12 is shaped as a sleeve/funnel having an outer diameter of 3-7 mm, a length of 2-5 cm and a volume of 0.14-2 cm$^3$. When collapsed, elongated braid structure 12 is constrained to an outer diameter of 1.5-3 mm and a length of 2-7 cm.

Elongated braid structure 12 is composed of 6-24 wires 30 with each wire 30 forming a loop 32 (6-12 loops 32). Wires 30 can be 0.025-0.1 mm in diameter and made of an alloy such as NITINOL or stainless steel or from a polymer such as polyethylene or polypropylene. Tails 34 of each looped wire 30 are counter-wound in a helical pattern in a distal to proximal direction. The formed braid includes a crisscrossing pattern of wires 30 forming a mesh with angles between crossing wires 30 ranging between 70-140 degrees.

Portion 31 of wires 30 can be thinner than portion 33 thereby enabling greater compliance in loops 32 than the rest of elongated braid structure. For example, portion 33 of wires 30 can be 0.04-0.1 mm in diameter while portion 31 can be 0.025-0.05 mm in diameter.

Loops 32 form the distal end of elongated braid structure and are circumferentially positioned side-by-side in an overlapping pattern every 2 wires or every 3 or 4 wires. Loops 32 form a part of the closure mechanism of elongated braid structure 12. As is shown in the transition between the open and closed states of FIGS. 2A and 2B (respectively), pulling of loops 32 inward closed distal opening 22 of elongated braid structure.

Such closure can be facilitated by a closure wire 36 (highlighted by dashed line in FIG. 2A and shown at loops 32) that is actuated from handle 16. Closure wire 36 can be an alloy or polymer wire having a diameter of 0.025-0.25 mm and a length of 15-200 cm (handle 16 to braid structure 12). Closure wire 36 is preferably spiraled along the length of elongated braid structure and is position against the inner or outer walls thereof. As is mentioned hereinabove, spiraling of wire 36 is advantageous in that it negates any effects of bending of elongated braid structure 12 resulting from delivery through torturous vessels or changes in length of the braid structure. A wire run straight through elongated braid structure 12 would shorten and thus actuate closure of distal opening 22 when elongated braid structure 12 is bent (e.g. when delivered through or positioned in a curved vessel) or expanded/contracted.

Figure 2C:
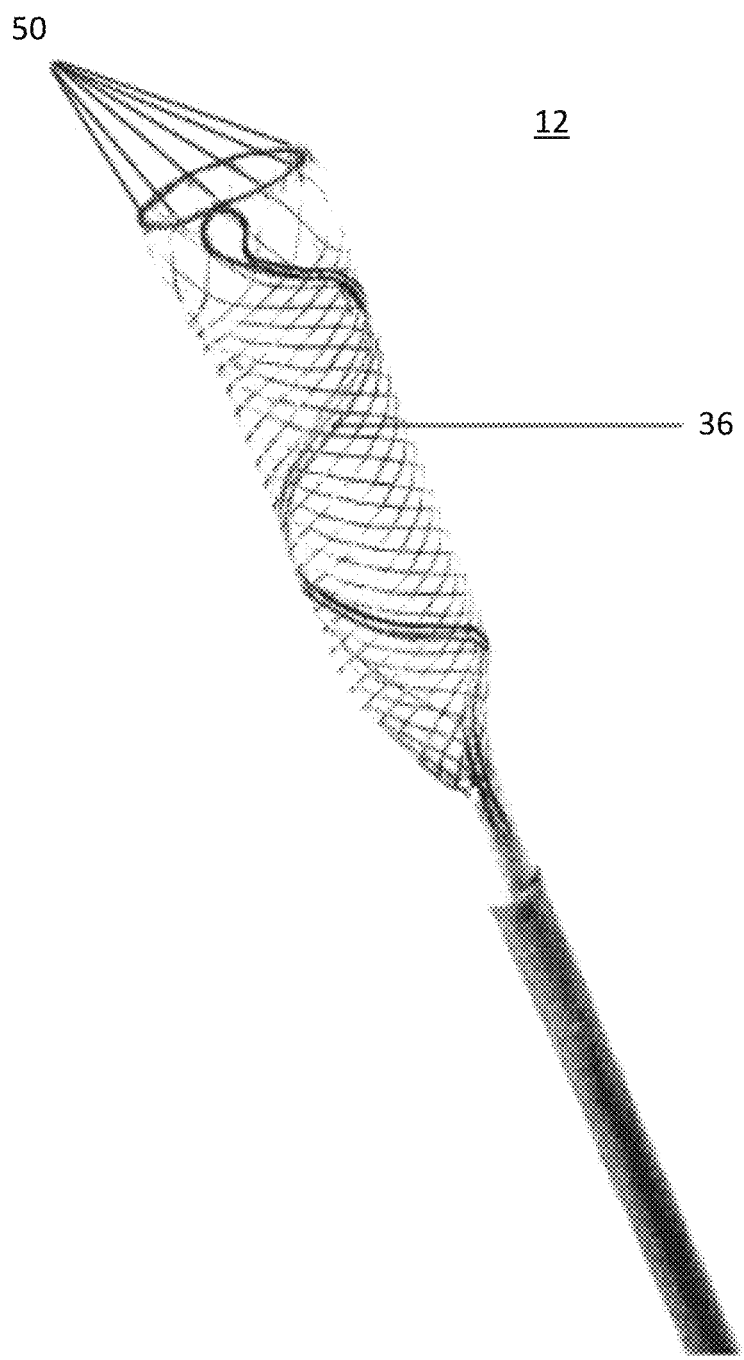
FIG. 2C is an isometric view of one embodiment of the elongated braid structure showing the spiraled closure wire threaded therein.

An embodiment of the present device in which closure wire 36 is spiraled along the length of elongated braid structure 12, threaded through eyelets 50 then threaded back along the length of elongated braid structure 12 is shown in FIG. 2C. In such a configuration of the present device, both ends of closure wire 36 are routed to the handle and attached to a single wire or directly to the actuation knob. This double spiral wire configuration increases reliability of distal opening actuation since the wire is attached in symmetric manner and friction in eyelets 50 is distributed more evenly. This decreases friction that can oppose full opening of the distal end as well as facilitates smoother operation when distal opening is pulled closed.

Elongated braid structure 12 is designed to conform with highly curved vessels and to be able to retrieve a large clot. It is also designed to arrest flow in the vessel when expanded and to prevent interaction between the clot and blood vessel once the clot is encapsulated.

Elongated braid structure 12 can also include radio-opaque markers (e.g. gold, Platinum or Tantalum) that allow an operator to identify the location of the funnel prior to expansion and during retrieval using fluoroscopy. According to one embodiments, at least one of the braiding wires can include a radiopaque core wire such as platinum inside the Nitinol wire (e.g., a DFT wire). A radiopaque crimp can be attached to one or more of the leaflet loops. The closure wire can also be a DFT wire.

Elongated braid structure 12 can be coated (internally or externally) with a thin and compliant polymeric cover 40 so as to enable an operator to aspirate a clot into the lumen of elongated braid structure 12 using suction source 17. Coating of stents and braided structures is well known in the art. It is done using various techniques such as dipping spraying or deposition. It usually combines a first step of coating the structure i.e. the structure struts with a very thin layer and a second step of mounting the structure on a mandrel and coating the mandrel to cover the cells between struts and to form a cylindrical coating.

Since coat 40 can have a significant effect on performance (e.g., bendability of braid 12) it is preferably fabricated from a compliant material such as polyurethane that is 5-30 micron thick.

Elongated braid structure 12 covered with coat 40 can exhibit very high elasticity. Elasticity of the coating is mainly important for transition between compressed and expanded configuration. The cells of the braided structure are diamond shape. The cells axial axis (along the braided structure axis) elongate by 100% or more when the braided structure is compressed into the outer sheath and the polymer coating should allow such elongation without tearing.

A lumen can be formed along the length of an internal or external surface of elongated braid structure 12 (e.g. formed within coat 40). Such a lumen can be connected to handle 16 via a conduit running the length of catheter shaft 14. The lumen can be used to administer contrast media into the blood vessel lumen in order to identify clot presence without interfering with the clot position.

The expanded diameter of elongated braid structure 12 is configured slightly larger than that of the blood vessel throughout its length or at loops 32. This ensures a tight seal between elongated braid structure 12 and the vessel walls and occlusion of blood flow. Such occlusion prevents aspiration of "clean" blood flowing into the clot site, enhances clot aspiration and prevents clot particles from flowing past elongated braid structure 12.

Loops 32 can be rounded or triangular in shape (or any other suitable shape) and are 1-4 mm long (e.g., 3 mm) and 2*PI*D/number of loops wide at the base (regions of first wire crossing).

Loops 32 can flare outward or be continuous with the wall of elongated braid structure 12.

Each loop 32 or some of loops 30 can include an eyelet 50 for routing of closure wire 36 therethrough. Eyelet 50 can be oriented with its axis tangential to elongated braid structure 12 (e.g. 90 rotated 90 degrees with respect to the plane of loop 32), such that closure wire 36 can be threaded thru eyelets 50 to form a circle that can be cinched-closed while reducing the friction between wire 36 and loops 32 which in turn reduces the pulling force required to close loops 32. In order to reduce friction, coat 40 can end at loops 32 and does not cover eyelets 50.

Eyelets 50 can be formed by twisting ends of loops 32 or by welding/soldering eyelets 50 to ends of loops 32.

Figure 5:
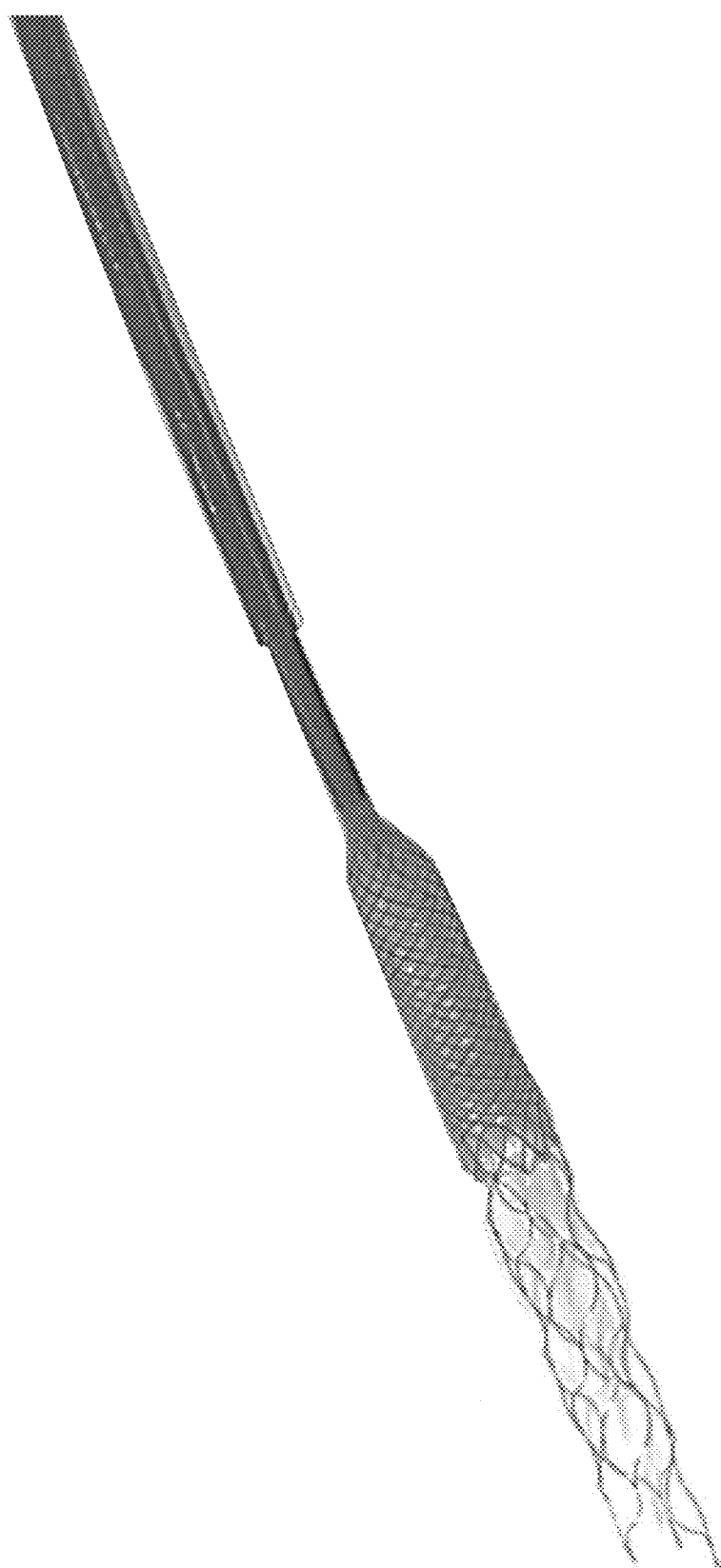
FIG. 5 illustrates stent retrieval using the present prototype.

The present system can be used to retrieve biological material such as clots or objects such as stents (FIG. 5).

The following describes use of the present system in retrieval of a clot from a blood vessel such as an artery using a percutaneous approach.

Figure 3A:
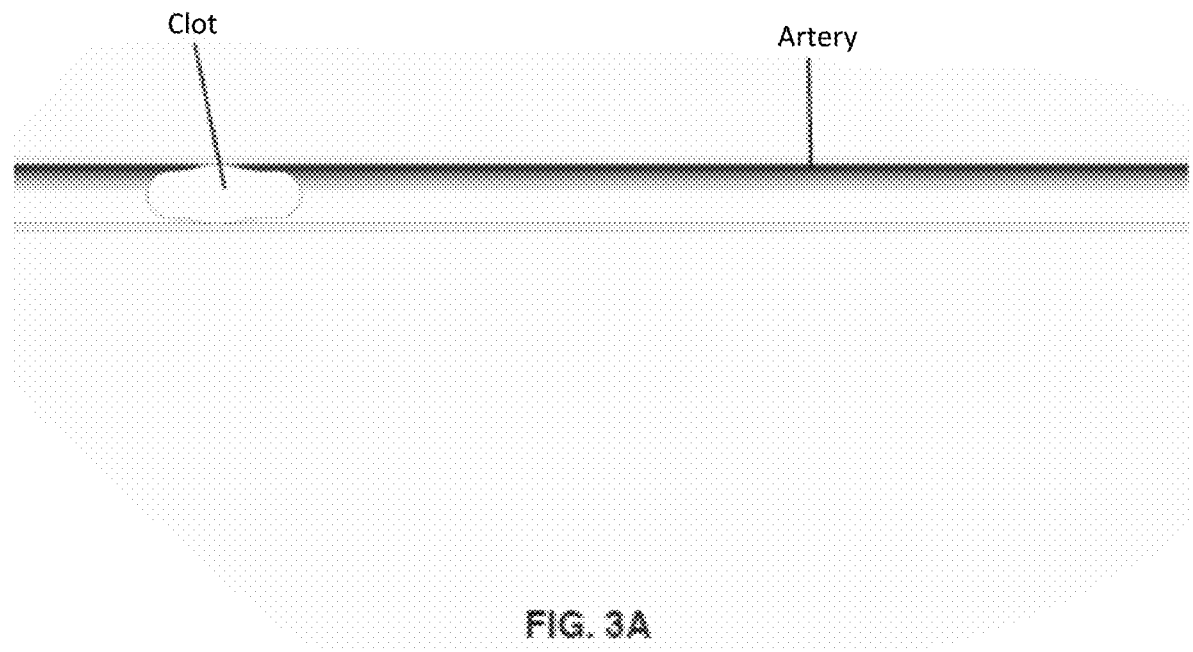
FIGS. 3A-3E illustrate steps of a clot retrieval process using one embodiment of the present system.
Figure 3B:
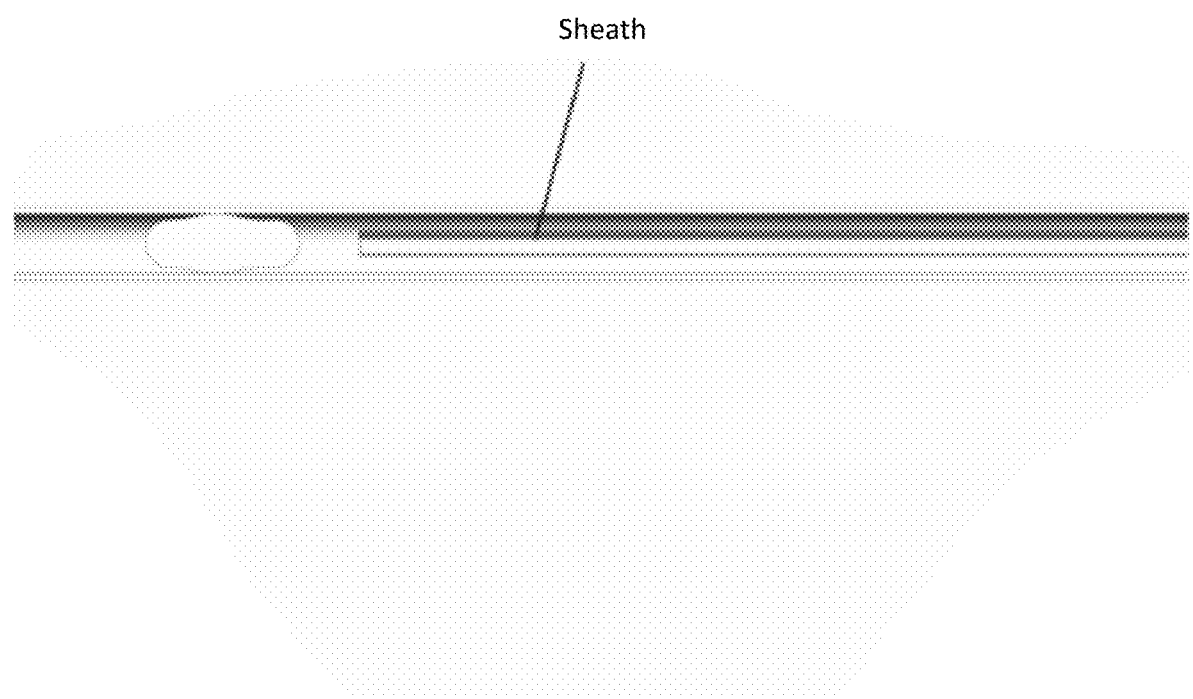
Figure 3C:
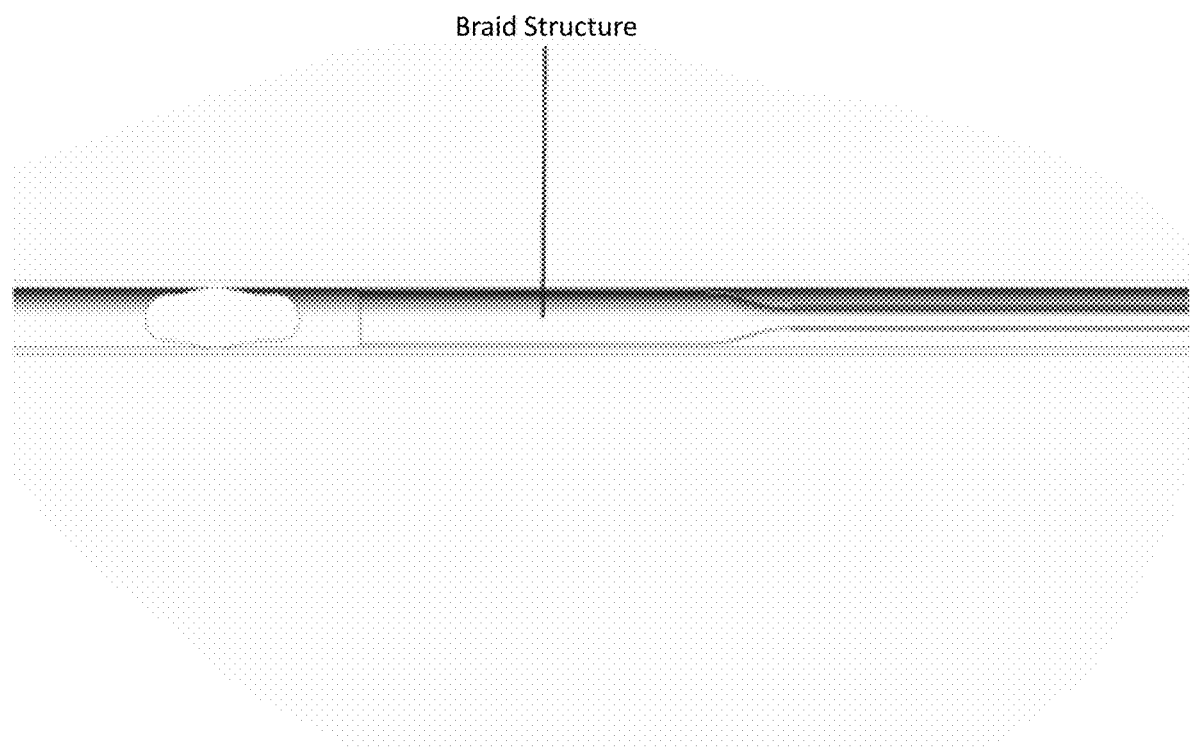

A guide catheter or guiding sheath is positioned in the internal carotid artery and the present system is delivery as a tri-axial system over a microcatheter with guide wire (GW). The present system is navigated over the microcatheter-GW under fluoroscopy with the braid structure collapsed inside the sheath until the distal end of the sheath is proximal to the clot (FIG. 3A-B), The operator pulls the sheath while advancing the catheter shaft to deploy the elongated braid structure and allow it to self-expand up to the vessel diameter and shape (FIG. 3C) thus arresting the blood flow in the artery.

Figure 3D:
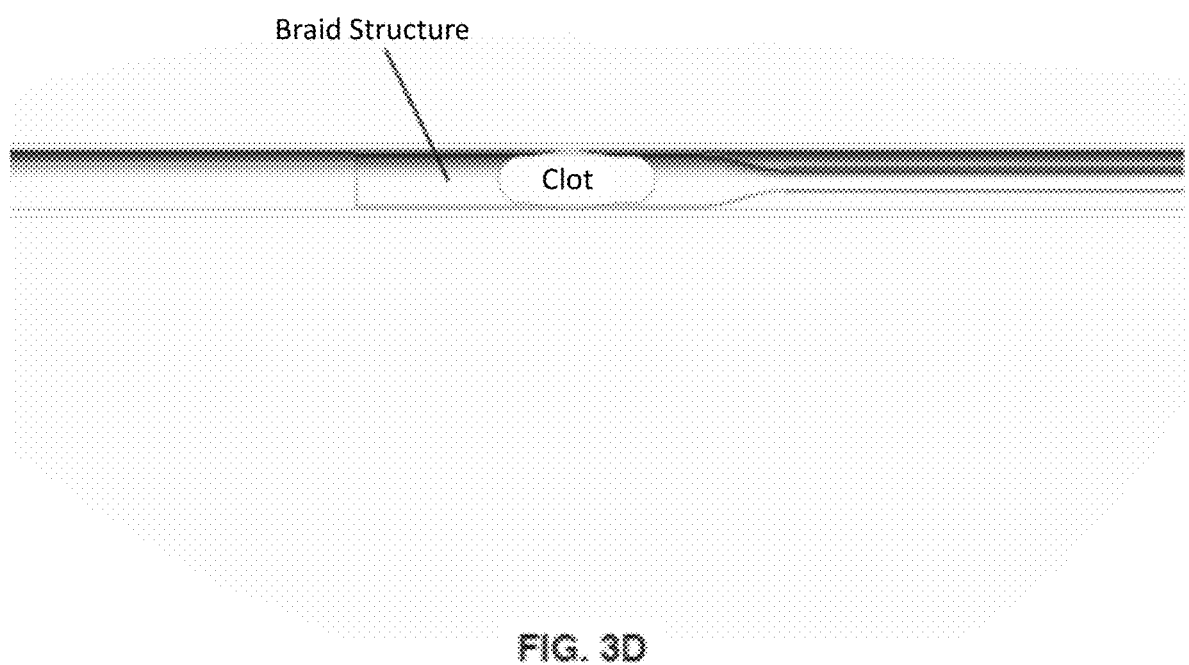

The operator retracts the microcatheter-GW, and connects a syringe or pump to the handle proximal end. The syringe/pump is used to aspirate the clot into the funnel (FIG. 3D). Alternatively a stent retriever (FIG. 5) is used to retrieve the clot following which the stent retriever and clot are aspirated or captured by the present device.

Figure 3E:
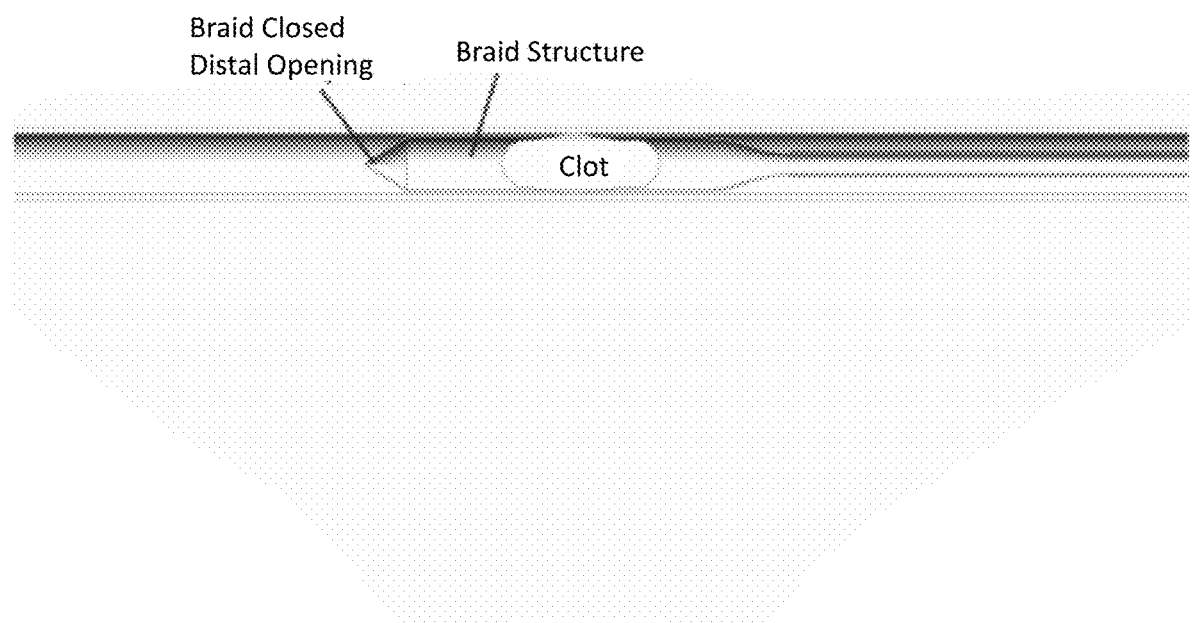

When the clot is fully retrieved into the braid structure (FIG. 3D) the operator rotates a knob in handle to close the distal opening of the braid structure to encapsulate the clot (FIG. 3E)

The braid structure is then retracted into the sheath and the system is removed from the body. The operator can then inject a contrast agent through the catheter to verify that the clot is removed.

Alternatively, elongated braid structure 12 can be deployed in contact with the clot, distal opening 22 can then be partially closed (via partial pull of closure wire 36) to form a tapered tip. Vacuum can then be applied to aspirate the clot into the lumen of elongated braid structure 12 following which, distal opening 22 can be fully closed and the catheter retracted from the blood vessel.

Braiding the elongated structure is preferred since it results in a tube structure that is characterized by axial flexibility and is therefore highly adaptable with curved anatomies. However other techniques such as laser cutting of tubes can be used for less curved anatomies, or if future advancement in these technologies improve the axial flexibility performance Laser cutting from a tube would use patterns similar to those used for self-expanding stents, including an axial array of zigzag rings interconnected with bridges. In order to make loops 32 more compliant in a laser cut elongated structure, they can be cut with a narrower profile than the rest of the elongated structure.

Due to its distal end closure capabilities, the present device can also be used to snare large and hard clots that has high friction with the vessel wall cannot be fully aspirated into the braid structure. In such cases, the leaflets can be closed over the clot to bite into the clot material and snare the clot out of the body.

The leaflets of the braid structure can also be used to biopsy tissue. In such cases, the loop wire can be profiled to enable tissue cutting such that when the distal end is closed over a tissue, a portion of the tissue can be cut and retrieved into the braid structure.

As used herein the term "about" refers to ±10%.

EXAMPLES

Reference is now made to the following examples, which together with the above descriptions, illustrate the invention in a non limiting fashion.

Example 1

Fabrication of the Braid Structure

Figure 4A:
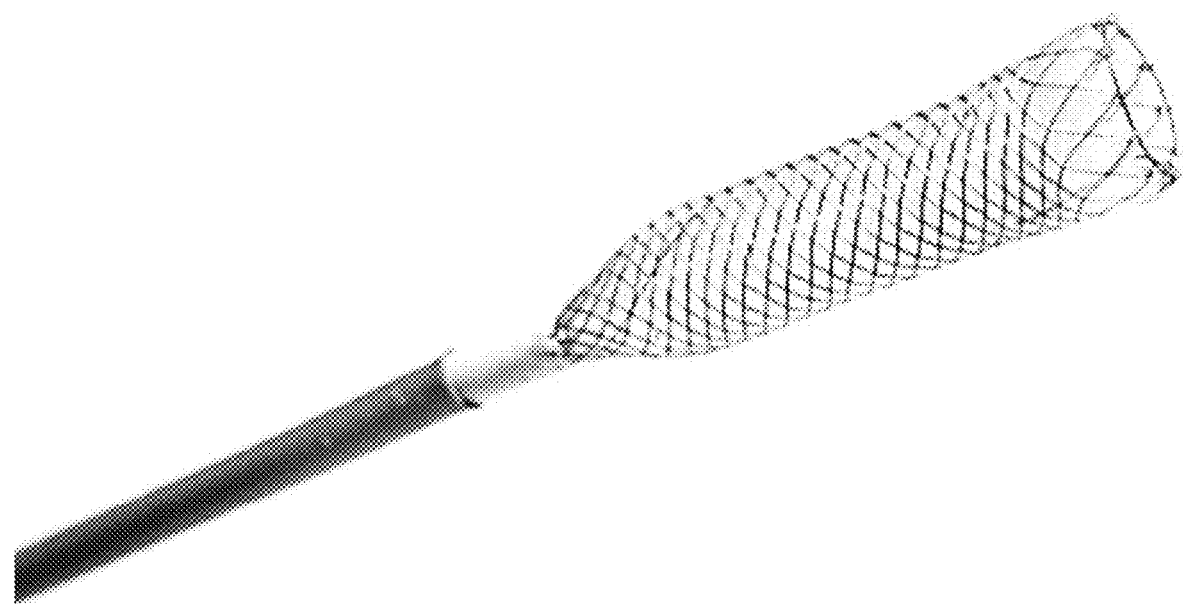
FIG. 4A illustrates a prototype of the present elongated braid structure in an expanded open state.
Figure 4B:
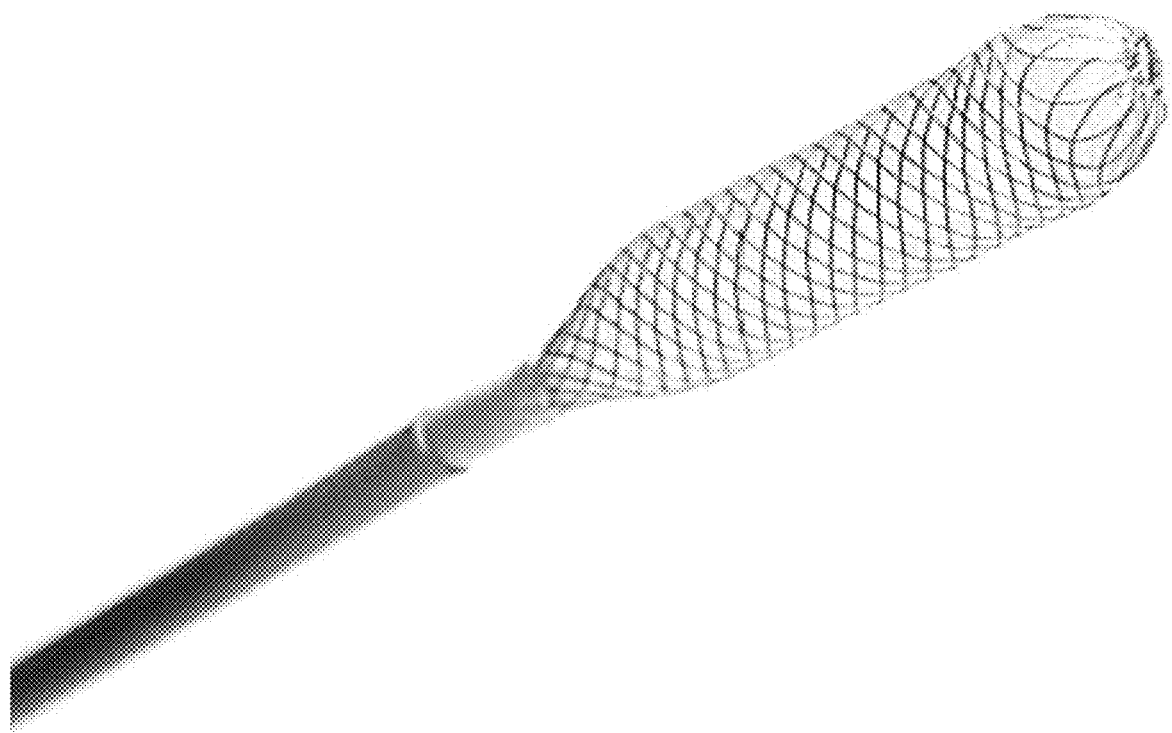
FIG. 4B illustrates a prototype of the present elongated braid structure in a closed state.
Figure 4C:
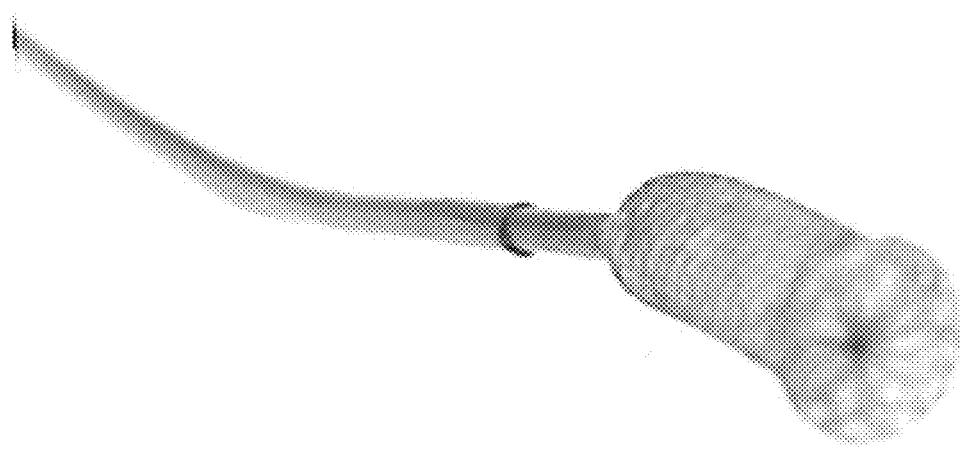
FIG. 4C illustrates a prototype of the present elongated braid structure in a closed-inverted state.

The elongated braid structure shown in FIGS. 4A-C was fabricated from 9 nitinol wires Diameter 0.06 mm and 3 DFT wires. The technician mounted the wires in dedicated jig, generating the eyelets, then crossing the wires to generate the distal loops, then crisscrossing the wires to generate the braid structure. Then the structure was heat treated to keep its shape. The handle, shaft and sheath were manufactured separately.

The braid structure then coated in polyurethane thin layer 0.020 mm by dipping.

The closure wire is heat treated to the suitable shape using special jig. Then threaded into the funnel distal loops eyelets and fixed in one end. Then the wire is placed inside the funnel and threaded into the shaft side lumen from the distal end until the proximal end and connected to the handle.

The elongated braid structure was then connected to the shaft using a fusion process.

Closure and opening of the braid structure was successfully tested by pulling/releasing (respectively) the proximal end of the closure wire (FIGS. 4B and 4A respectively). Pulling of the closure wire to achieve an inward inverted closure was also successfully tested (FIG. 4C).

Example 2

Animal Study

An animal trial using a Porcine model (female, 49 kg) was conducted to test a prototype of the present device in clot removal and preventing distal embolization.

Several prototypes were used to evaluate sheath design, sheath materials and radiopaque markers.

Autologous blood was taken from the animal prior the study and used to create a whole blood thrombus by mixing whole blood with barium sulfate for radiopacity and incubating the mixture at room temperature for one hour. The thrombus was then injected through a guiding catheter to the selected vessel (common carotid branch). The clot position was inspected by contrast media injection under fluoroscopy (Angiograph).

Results

Figure 6:
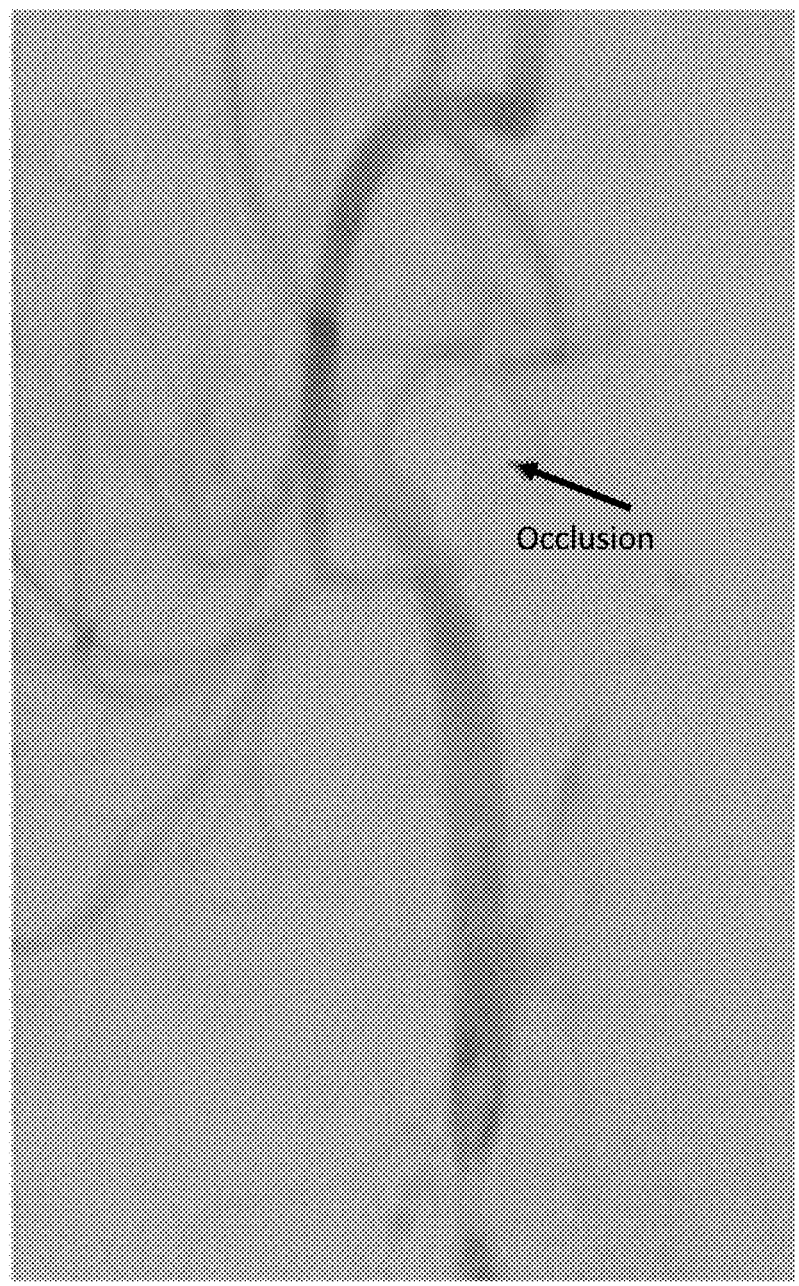
FIG. 6 is an angiographs illustrating clot retrieval using a prototype of the present system.
Figure 7:
FIG. 7 is an angiographs illustrating clot retrieval using a prototype of the present system.

The present system was navigated to the occluded site in the common carotid branches until the sheath tip was positioned proximal to the clot. The sheath was retracted until the funnel was fully deployed. A 30 cc syringe was connected to the catheter hub and the syringe plunger was pulled slowly to generate vacuum and aspirate the clot. Once the clot was visualized in the braid structure (FIG. 6) the knob on handle of the catheter was rotated to close the wire loops (leaflets). Closure was visualized with the leaflets collapsed into the braid structure. The braid structure was retracted into the guiding sheath and the catheter was removed from the body. No clot fragments were released out of funnel. An angiograph was performed to verify recanalization of the artery (FIG. 7).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for retrieving material or objects from a biological vessel comprising: (a) an elongated braid structure including a plurality of helically wound wires crossing a plurality of counter-helically wound wires wherein at least some of said plurality of helically wound wires cross said plurality of counter-helically wound wires at an angle of 70-120 degrees, wherein a distal end of said elongated braid structure forms a plurality of wire loops and a distal portion of said elongated braid structure includes eyelets, and wherein said eyelets are in a different plane than a plane of said plurality of wire loops, said elongated braid structure configured for transitioning between collapsed and expanded states, said elongated braid structure surrounding a lumen having a distal opening when in said expanded state; and (b) a closure wire positioned along a length of said elongated braid structure, said closure wire being actuatable to pull inward said distal portion of said elongated braid structure and thereby at least partially close said distal opening; wherein said closure wire is positioned such that said distal portion of said elongated braid structure is not pulled inward when said elongated braid structure is bent along said length.

2. The system of claim 1, wherein said closure wire is spiraled along said length of said elongated braid structure.

3. The system of claim 1, wherein said closure wire runs through at least some of said eyelets.

4. The system of claim 1, wherein each of said plurality of wire loops interconnects a helically wound wire to a counter-helically wound wire.

5. The system of claim 1, wherein said plurality of wire loops cross each other.

6. The system of claim 1, further comprising a catheter attached to said elongated braid structure.

7. The system of claim 6, wherein a distal portion of said catheter includes a sheath and said elongated braid structure is maintainable in said collapsed state within said sheath.

8. The system of claim 7, wherein said elongated braid structure self-expands when said sheath is retracted.

9. The system of claim 1, wherein said elongated braid structure includes a cover.

10. The system of claim 9, wherein said closure wire is trapped between said braid structure and said cover or embedded within said cover.

11. The system of claim 1, wherein a wire portion forming a loop of said plurality of wire loops is more compliant than a second wire portion forming said elongated braid structure proximal to said plurality of wire loops.

12. The system of claim 1, wherein each of said plurality of wire loops angles outward from said distal opening.

13. A system for retrieving material or objects from a biological vessel comprising an elongated braid structure configured for transitioning between collapsed and expanded states, said elongated braid structure surrounding a lumen having a distal opening when in said expanded state; wherein said elongated braid structure includes a plurality of helically wound wires crossing a plurality of counter-helically wound wires forming a plurality of wire loops around said distal opening of said elongated braid structure, wherein a distal portion of said elongated braid structure includes eyelets, and wherein said eyelets are in a different plane than a plane of said plurality of wire loops.

14. The system of claim 13, wherein each of said plurality of wire loops interconnects a helically wound wire to a counter-helically wound wire.

15. The system of claim 13, wherein said plurality of helically wound wires cross said plurality of counter-helically wound wires at an angle of 70-120 degrees.

* * * * *